United States Patent
Estes et al.

(10) Patent No.: US 9,909,927 B1
(45) Date of Patent: Mar. 6, 2018

(54) OPTICAL ATTENUATION COEFFICIENT METER

(71) Applicants: Lee E Estes, Mattapoisett, MA (US); Stephen B Doyle, Wakefield, RI (US)

(72) Inventors: Lee E Estes, Mattapoisett, MA (US); Stephen B Doyle, Wakefield, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 40 days.

(21) Appl. No.: 15/189,038

(22) Filed: Jun. 22, 2016

(51) Int. Cl.
*G01N 21/47* (2006.01)
*G01J 11/00* (2006.01)

(52) U.S. Cl.
CPC ............ *G01J 11/00* (2013.01); *G01N 21/474* (2013.01)

(58) Field of Classification Search
CPC ......... G01N 2201/0218; G01N 21/255; G01N 21/538; G01N 2021/1793; G01N 21/65; G01N 21/8507; G01N 2201/0212; G01N 2201/0214; G01N 2291/0251; G01N 2291/02827; G01N 2291/02881; G01N 2291/0289
See application file for complete search history.

(56) References Cited

U.S. PATENT DOCUMENTS

| | | | | |
|---|---|---|---|---|
| 4,986,656 A * | 1/1991 | Sweeney | ................... | G01J 3/44 356/301 |
| 5,296,711 A * | 3/1994 | Leonard | ................. | G01N 21/65 250/253 |
| 5,457,639 A * | 10/1995 | Ulich | ...................... | G01S 7/487 356/5.1 |
| 5,822,047 A * | 10/1998 | Contarino | ............... | G01S 7/484 356/5.01 |
| 6,388,246 B1 * | 5/2002 | Fry | ......................... | G01S 7/487 250/221 |
| 6,608,677 B1 * | 8/2003 | Ray | ......................... | G01N 21/65 356/301 |
| 2011/0205536 A1 * | 8/2011 | Johnsen | .................... | G01J 3/06 356/326 |
| 2016/0238698 A1 * | 8/2016 | Vuorenkoski-Dalgleish | ................ | G01S 17/88 |

* cited by examiner

Primary Examiner — Michael P Stafira
(74) Attorney, Agent, or Firm — James M. Kasischke; Michael P. Stanley

(57) ABSTRACT

An attenuation meter is provided for use in a water environment. In operation, a transmitter of the meter transmits a laser pulse focused to a size at a predetermined range. A receiver of the meter images a focused spot to minimize unwanted light back scattering and avoid diffractive spreading within the back scattering region. Filtering the angular region can further reject scattered light. The filtered light is received, measured and processed by a oscilloscope as pulse averages. The meter also includes a photodetector to measure a diffuse attenuation coefficient. The output voltage of the photodetector is measured and processed by the oscilloscope that produces an average voltage over a preset number of pulses. A controller best fits voltage to time dependence to produce the diffuse attenuation coefficient. Only the shape of the receiver time dependence is required to provide the diffuse attenuation coefficient measurement.

6 Claims, 2 Drawing Sheets

OPTICAL ATTENUATION COEFFICIENT METER

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

(1) Field of the Invention

The present invention is a meter and method of use for measuring an optical beam attenuation coefficient and an optical diffuse attenuation coefficient in a liquid medium. The beam attenuation co-efficient accounts for the loss of a narrow, collimated beam of monochromatic light by absorption and scattering per unit distance while the diffuse attenuation co-efficient accounts for absorption loss from both direct and scattered paths of a directional light field.

(2) Description of the Prior Art

Numerous commercial meters are available to measure an optical beam attenuation coefficient "c" and a diffuse attenuation coefficient "K" in water. To limit size, the meters use optical propagation paths that are generally less than 1 meter in length. In clear water, the attenuation lengths (1/attenuation coefficient) are often greater than eight meters. This circumstance imposes demands on the cleanliness of the optical surfaces, the accuracy of the measuring electronics, and the accuracy of the calibration procedures. The demands include the avoidance of absorption and scattering in the meter. Because of this circumstance, the measurements provided by the meters in clear water are generally non-repeatable and inaccurate to the extent that the measurements are generally unusable.

As such, there is a need for a meter, recognizing back scattering by a pulsed laser source, that would allow a propagation path, which is not confined by the size of the meter.

SUMMARY OF THE INVENTION

Accordingly, it is a general purpose and primary object of the present invention to provide an attenuation meter for measurements of an optical beam attenuation coefficient in a water environment.

It is a further object of the present invention to provide an attenuation meter for measurement of an optical diffuse attenuation coefficient in a water environment.

It is a still further object of the present invention to provide an attenuation meter for measurements of an optical beam attenuation coefficient in a liquid medium.

It is a still further object of the present invention to provide an attenuation meter for measurement of an optical diffuse attenuation coefficient in a liquid medium.

In order to attain the objects described, an attenuation meter with a transmitter and receiver is provided in which the transmitter produces a laser pulse of a duration and in-water wavelength that is focused to a sized location at a range from the attenuation meter. As the laser pulse propagates thru water, some of the light becomes back scattered. A partial rejection of the back scattered light is achieved by filtering an angular region to only admit light back scattered within a calculated solid angle. The time bandwidth of receiver detection is set so that the receiver response time matches the pulse width.

An output sample from the receiver is averaged over numerous pulses; thereby, allowing for multiple and independent scattering realizations to produce an average output result. The laser output can then be focused to a sized location at a larger and different range to produce an average output result. The beam attenuation coefficient of the water is then calculated by using this time average.

The laser of the transmitter produces nanosecond pulses of linearly polarized light at a predetermined repetition rate. A lens of the transmitter collimates the light and a half wavelength plate rotates the polarization of the light until the light polarization is horizontal. Mirrors direct the light onto a lens that focuses the light to a 50 micron diameter in the plane of a pinhole. Lenses project a virtual image of a plane of the pinhole in a region between a negative lens and a positive lens.

The light output passes through a quarter waveplate that converts the light to a circular polarization. The light then forms an image in the water. Light that is back scattered in a region about the sized location is reflected back to the receiver. To the extent that the circular polarization is preserved; the back scattered light is converted to linear polarization by the quarter waveplate in that the returning light is directed to the receiver.

When the back scattered light reaches a polarized beam splitter, the light is reflected toward a mirror. A small portion of the output light is reflected toward a high speed detector that can calculate the duration of the laser pulses. The output of the high speed detector is sent to a channel of a Pico Scope (a portable oscilloscope). The output of the high speed detector is measured and recorded at the Pico Scope to validate the laser pulse strength and time wave shape.

A unit magnification image relay telescope images the water focal region onto a pinhole. The comparatively small size of the pinhole is matched to an ideal pinhole image formed in the water. This matched filtering rejects light that was forward scattered into regions outside the ideal water image. Another pinhole is positioned in the far field of the first pinhole. The size of the pinhole is matched to the angular region of light that is used to focus onto the first pinhole. Thus, the pinhole also rejects multiple scattered light.

To further reject background light, an interference filter (tuned to the laser light wavelength) is positioned at the detector. The output of the detector is measured, recorded, and processed by the Pico Scope to form multiple pulse averages that are then accessed by a PC104 controller for processing and storage.

After a preset time interval (determined by the desired number of pulses to be averaged); the PC104 controller commands a translator controller to move the telescope in order to focus the light at a different range and position. When the results for the times for different ranges are processed; the PC104 controller divides the results to generate a result that can be used to calculate the beam attenuation coefficient.

A photodetector measures the diffuse attenuation coefficient. In operation, the output voltage of the photodetector is measured and processed by the Pico Scope that produces an average voltage over a preset number of pulses. Next, the voltage is sent to the PC104 controller where the output voltage is recorded and processed. The controller makes a best fit of voltage to calculated time dependence in order to produce a measurement of the diffuse attenuation coefficient.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

Figure 1:
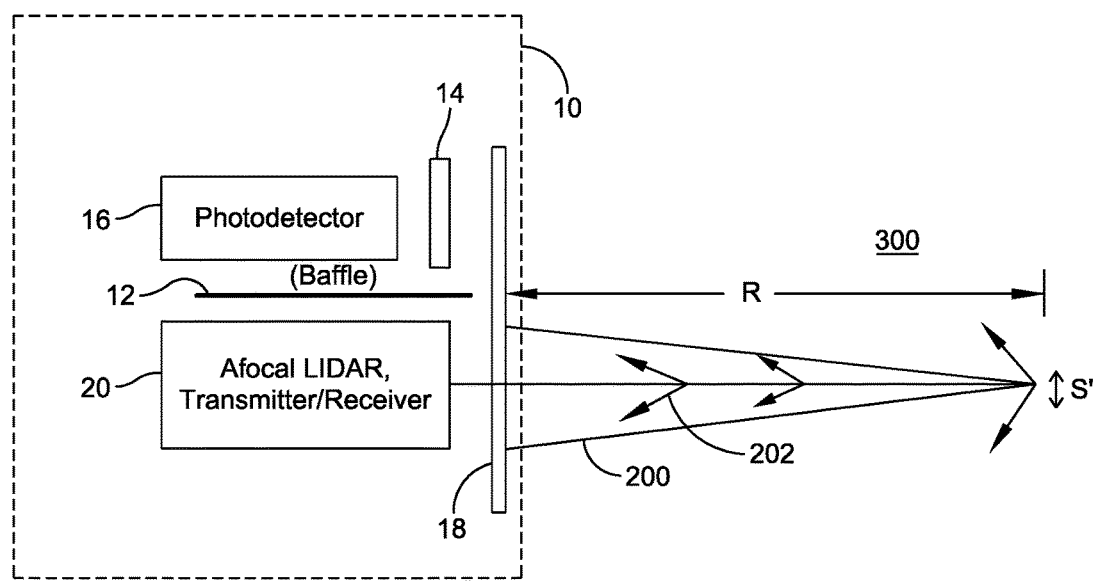
FIG. 1 is a depiction of an attenuation meter of the present invention operating in a water environment.

An attenuation meter 10 and a water environment 300 to be measured are depicted in FIG. 1. In the figure, the attenuation meter 10 comprises an afocal LIDAR transmitter/receiver 20 (with a lateral magnification M and a longitudinal magnification $M^2$) which transmits a laser pulse 200 of duration, $\tau$, and in-water wavelength, $\lambda_W$, that is focused to a location with a size, S (the diameter of the laser pulse at the image), at a range, R.

As the laser pulse 200 propagates thru the water 300, some of the light becomes back scattered light 202. The back scattered light 202 travels to the attenuation meter 10 after scattering by thermodynamic density fluctuations and particles within the water 300. The back scattered light 202 is from a focused spot or location in the water 300 or liquid medium. At any time, $t > \tau$, light that is scattered only once in the backward direction is scattered within a range segment that is $$\frac{c_W \tau}{2} \tag{1}$$

where $c_W$ is the speed of light at the wavelength of the laser in the liquid medium.

A receiver component of the transmitter/receiver 20 images the focused spot or location onto a hole (aperture) of size $$S/M. \tag{2}$$

This imaging minimizes light that undergoes multiple scattering. To avoid the effects of diffractive spreading within a back scattering region of interest; the spot size is chosen so that $$S^2 \geq \frac{c_W \tau \lambda_W}{2}. \tag{3}$$

If the transmitted pulse begins at the time, t=0; the received signal at the time t is due to light scattered within the ranges $$\frac{c_W(t-\tau)}{2} \leq R \leq \frac{c_W t}{2} \tag{4}$$

which provides a range resolution of $$\Delta R = \frac{c_W \tau}{2}. \tag{5}$$

The time bandwidth of the transmitter/receiver 20 is set so that the response time of the back scattered light matches the pulse width or pulse duration, $\tau$. An output telescope is mounted on a motorized translation stage (not shown) so that the laser pulse 200 can be focused at different ranges. For the fixed focal range, $R_1$; the output of a photodetector 16 of the attenuation meter 10 is sampled at $$t = \frac{2R_1}{c_W} + \frac{\tau}{2}. \tag{6}$$

A sampled output pulse power, $P_1$, is averaged over numerous pulses; thereby, allowing numerous independent scattering realizations to produce an average result, $\overline{P}_1$. The laser output is then focused to the same size, S, at a different range, $R_2 > R_1$, to produce an average result $\overline{P}_2$. The beam attenuation coefficient, c, of the water can then be determined by $$c = \frac{1}{2(R_2 - R_1)} \ln\left(\frac{\overline{P}_1}{\overline{P}_2}\right) \tag{7}$$

Figure 2:
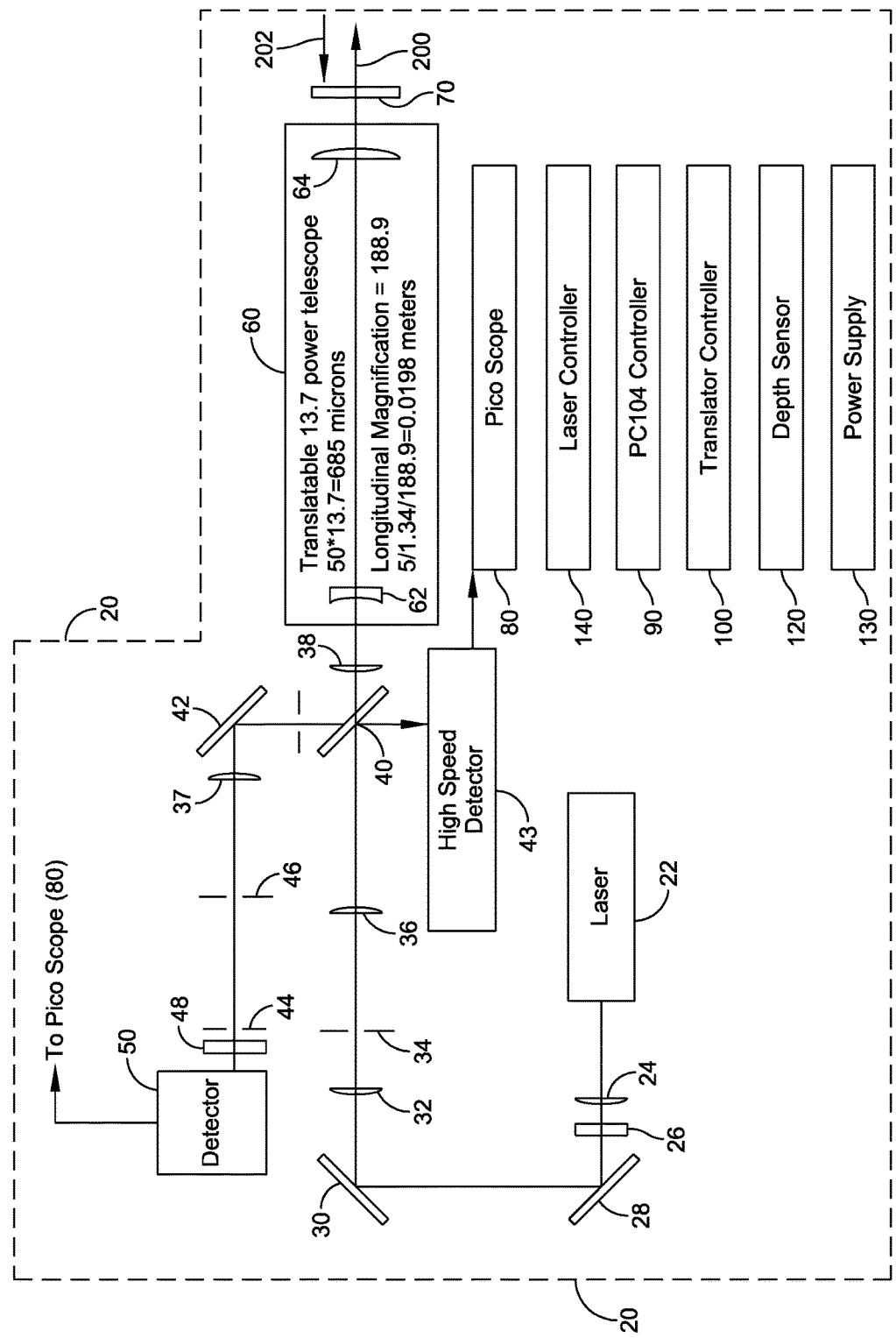
FIG. 2 is a schematic of associated components of the optical attenuation meter of the present invention.

FIG. 2 depicts a detailed design of the afocal LIDAR transmitter/receiver 20. In the figure, a microchip laser 22 produces one nanosecond (ns) duration pulses of linearly polarized light at a 532 nanometer (nm) vacuum wavelength and a 6 kHz repetition rate.

A first lens 24 collimates the light and a half wavelength plate 26 rotates the polarization of the light to horizontal. A first mirror 28 and a second mirror 30 direct the light onto a second lens 32 that focuses the light to a 50 micron diameter in the plane of a 50 micron diameter pinhole (aperture) of a first section 34. A third lens 36 and a fourth lens 38 form a first unit magnification image relay telescope that projects a virtual image of the pinhole of the first section 34 to a power telescope 60 of a region between a negative lens 62 (first power telescope lens) and a positive lens 64 (second power telescope lens). In the example shown in FIG. 2; a transverse magnification of the telescope 60 is M=117 and the longitudinal magnification is $M^2$=188.9.

The light output of the telescope 60 passes through a quarter waveplate 70 that converts the light pulse to a circular polarization. The light pulse then forms an image of size S=13.7*50=685 microns in the water 300. Light that is back scattered in the region $$\frac{c_W \tau}{2} = \frac{3 \times 10^8}{1.34} \times 10^{-9}/2 = 0.11 \text{ meters} \left( < \frac{S^2}{\lambda_W} = 1.18 \text{ meters} \right)$$

about the focus of the light pulse is reflected back to the transmitter/receiver 20. To the extent that the circular polarization is preserved; the back scattered light is converted to linear polarization by the quarter waveplate 70, which is rotated ninety degrees from the outgoing light that enters the waveplate.

When the back scattered light 202 reaches a first polarized beam splitter 40, the back scattered light is reflected toward a third mirror 42. For the outgoing light, the light polarization is such that the light is transmitted by the first beam splitter 40. Also, when the outgoing light strikes the first beam splitter 40; a portion of the light is reflected (due to surface reflections and polarization errors) toward a high speed detector 43. The output of the high speed detector 43 is sent to a channel of a Pico Scope 80 (portable oscilloscope).

The output of the high speed detector 43 is measured and recorded at the Pico Scope 80 to validate the laser pulse strength (which is proportional to the output and time wave shape). The telescope 60 and a second unit magnification image relay telescope formed by a fifth lens 37 and the fourth lens 38; image the water focal region onto a pinhole (aperture) of a second section 46 via the fifth lens 37. The 50 micron size of the pinhole of the second section 46 is matched to an ideal image formed in the water 300. This matched filtering rejects light that was forward scattered into regions outside the ideal water image.

A pinhole (aperture) of a third section 44 is positioned approximately in the far field of the pinhole of the second section 46. The size of the pinhole of the third section 44 is matched to the angular spectrum of light that would be reflected by a perpendicular mirror placed at the water focal plane when no scattering takes place. Thus, the pinhole of the third section 44 further rejects multiple scattered light.

To additionally reject background light, an interference filter 48 (tuned to the laser light wavelength) is positioned at a detector 50. The output of the detector 50 is measured, recorded, and processed by the Pico Scope 80 to form multiple pulse averages which are then accessed by a PC104 Controller 90 for final processing and storage by implementation of Equation (7).

Because of the (matched filters) of the third section 44 and the second section 46; the average recorded output is approximately proportional to exp(−2cR). After a preset time interval (determined by the desired number of pulses to be averaged); the PC104 controller 90 commands a translator controller 100 to move the telescope 60 in order to focus the light at a different range or position.

In the example and using the components of FIG. 2, the range difference is chosen to be five meters which causes a ten meter difference in light propagation distance. In a vacuum, the five meter difference is reduced by the water index of refraction, n=1.34; thereby, producing a vacuum focal difference of 5/1.34=3.73 meters. For the longitudinal magnification of $M^2$=188.9, the telescope 60 must be translated 3.73/188.9=0.0197 meters. When the results for the times $$t = \frac{2R}{c_W} + \frac{\tau}{2}$$

for the different ranges are processed; the PC104 controller 90 divides the two results to generate $\overline{P}_1/\overline{P}_2$ which can be used along with $R_2-R_1$=5 meters in Equation (7) to determine the beam attenuation coefficient, c, at the 532 nm wavelength.

Returning to FIG. 1, the photodetector 16 is used to measure the diffuse attenuation coefficient, K. The interference filter 14 is tuned to the laser wavelength in order to discriminate against background light. For times t≫τ and pulse durations that satisfy $$\tau < \frac{1}{2Kc_W}; \qquad (8)$$

the back scattered optical power, $P_D(t)$, that reaches the photodetector 16 is approximately given by $$P_D(t) = \frac{TAE_P b_{180°} c_W \exp(-Kc_W t)}{\left(\frac{c_W t}{2}\right)^2}. \qquad (9)$$

where T is the combined transmission of the filter 14 and a window 18, A is the area of photosensitive portion of the photodetector 16, $E_P$ is the pulse energy, and $b_{180°}$ is the volume scattering coefficient in the backward direction at the laser light wavelength.

The output voltage, $V_D(t)$, of the photodetector 16 is given by $V_D(t)=gP_D(t)$ where g is the overall gain of the photodetector. $V_D(t)$ is then measured and processed by the Pico Scope 80 that produces an average, $\overline{V}_D(t)$, over the preset number of pulses. Next, $\overline{V}_D(t)$ is sent to the PC 104 controller 90 where the output voltage is recorded and processed. The PC 104 controller 90 makes a best fit of $\overline{V}_D(t)$ to the time dependence in Equation (9) to produce the measurement of K.

In FIG. 1, a baffle 12 is used to avoid light scattered within the attenuation meter 10 and at the window 18. The relative position of the photodetector 16 and the baffle 12 can be used to reduce the signal at the photodetector due to intense light that is back scattered at short ranges. If the short ranges are obstructed, $\overline{V}_D(t)$, must be compared with Equation (9) in the unobstructed region.

Returning to FIG. 2, a depth sensor 120 is used to activate the attenuation meter 10 after the meter has reached a desired depth to avoid surface effects. A power supply 130 is used to supply power to the components of the attenuation meter 10 that require power including a laser controller 140 that activates the laser 22.

A major advantage of the attenuation meter 10 is long measurement paths that allow for more accurate measurements than those provided by currently-available meters with short optical paths. Another advantage is that the beam attenuation measurement is derived from the sensor response by evaluating the ratio of the responses at two or possibly more ranges. This evaluation eliminates the calibration needed for conventional meters.

In the case of the diffuse attenuation coefficient; only the shape of the receiver time dependence and not the absolute level is required to provide the diffuse attenuation coefficient measurement by fitting the results of Equation (9). This comparison is accomplished by comparing the logarithms of Equation (9) and the logarithm detected signal. Yet another advantage is that the optical path length is easily adjusted to accommodate media with different clarity by adjusting the focal ranges with the controller 100.

The attenuation meter 10 can be deployed as a self-contained module and powered by appurtenant batteries and deployed on vehicles such as unmanned underwater vehicles (UUVs) or deployed from a separate platform with a cord connection that supplies electrical power and provides access to stored data. The attenuation meter 10 can contain more than a single color light source (preferably blue) to provide measurements at more than one wavelength.

The foregoing description of the preferred embodiments of the invention has been presented for purposes of illustration and description only. It is not intended to be exhaustive nor to limit the invention to the precise form disclosed; and obviously many modifications and variations are possible in light of the above teaching. Such modifications and variations that may be apparent to a person skilled in the art are intended to be included within the scope of this invention as defined by the accompanying claims.

What is claimed is:

1. An attenuation meter for measuring attenuation in a liquid medium, said meter comprising:
   a transmitter having a laser with said laser capable of transmitting a nanosecond light pulse to a location in the liquid medium with a predetermined lateral magnification M, longitudinal magnification $M^2$, pulse duration $\tau$, wavelength $\lambda_W$, focused size S and range R;
   a receiver operationally connected to said transmitter, said receiver capable of imaging a focused spot of back scattered light from the light pulse location in the liquid medium;
   a photodetector operationally to said receiver wherein said photodetector is capable of producing an output as a diffuse attenuation coefficient; and
   a baffle operationally positioned between said receiver and said photo detector wherein said baffle is capable of reducing light scattered within said attenuation meter.

2. The attenuation meter in accordance with claim 1, wherein said attenuation meter further comprises:
   a first lens operationally connected to said laser wherein said lens is capable of collimating the light pulse of said laser;
   a half waveplate operationally connected to said first lens on a side of said waveplate opposite to a side where said first lens is connected to said laser wherein said half waveplate is capable of rotating polarization of the light pulse to horizontal;
   a first mirror operationally connected to said half waveplate on a side of said waveplate opposite to a side where said waveplate is connected to said first lens;
   a second mirror operationally connected to said first mirror on a side of said first mirror opposite to a side where said first mirror is connected to said waveplate;
   a second lens operationally connected to said second mirror on a side of said second mirror opposite to a side where said second mirror is connected to said first mirror, said second lens capable of focusing the light pulse;
   a first section operationally connected to said second lens on a side of said second lens opposite to a side where said second lens is connected to said second mirror, said first section including an aperture sized for the focused light pulse from said second lens;
   a third lens operationally connected to said first section on a side of said first section opposite to a side where said first section is connected to said second lens;
   a first unit magnification image relay telescope including said third lens and a fourth lens as opposite ends of said first image relay telescope wherein said fourth lens is operationally connected to said third lens on a side of third lens opposite to a side where said third lens is connected to said first section;
   a power telescope having a first power telescope lens and a second power telescope lens as opposite ends of said power telescope with said first power telescope lens operationally connected to said fourth lens on a side of fourth lens opposite to a side where said fourth lens is connected to said third lens;
   a quarter waveplate operationally connected to said second power telescope lens on a side of second power telescope lens opposite to a side where said second power telescope lens is connected to said first power telescope lens, with said quarter waveplate capable of converting the pulse light to a circular polarization to form the pulse location in the liquid medium;
   a first beam splitter positioned in said first unit magnification image relay telescope with said first beam splitter between said third lens and said fourth lens;
   a high speed detector operationally connected to said first beam splitter with said high speed detector capable of detecting reflections and polarization errors of the light pulse;
   a second unit magnification image relay telescope formed by said fourth lens and a fifth lens as opposite ends, said fifth lens on a side opposite to said beam splitter connected to said high speed detector;
   a third mirror operationally connected to said beam splitter and said fifth lens, said third mirror positioned between said beam splitter and said fifth lens;
   a second section operationally connected to said fifth lens with said second section including an aperture, said second section positioned on a side of said fifth lens opposite to a side where said fifth lens is operationally connected to said third mirror;
   a third section operationally connected to said second section, said third section connected on a side opposite of said second section operationally connected to said fifth lens, said third section including an aperture on a far field of the aperture of said second section;
   a wavelength filter operationally connected to said third section on a side opposite of said third section connected to said second section;
   a detector operationally connected to said filter on a side of said filter opposite to a side where said filter is connected to said third section;
   an oscilloscope operationally connected to said high speed detector and said detector with said oscilloscope capable of validating strength of the light pulse and time wave shape from said high speed detector and the back scattered light from said detector; and
   a controller operationally connected to said oscilloscope;
   wherein back scattered light from the location in the liquid medium is convertible to vertical linear polarization by said quarter waveplate;
   wherein said second unit magnification image relay telescope is capable of imaging the back scattered light and the aperture of said second section is sized to match the image of the back scattered light;
   wherein said oscilloscope is capable of forming multiple pulse averages that are accessed by said controller to determine a beam attenuation coefficient based on a range and associated power of the light pulse.

3. The attenuation meter in accordance with claim 2, said meter further comprising a depth meter, said depth meter capable of activating said attenuation meter after reaching a predetermined depth in the liquid medium.

4. The attenuation meter in accordance with claim 3, wherein said aperture of said first section and said aperture of said second section are sized at 50 microns.

5. A method for measuring attenuation in a liquid medium, said method comprising the steps of:
   providing an attenuation meter having a transmitter, a receiver, a photodetector and PC 104 controller;
   setting a time bandwidth of the receiver so that a response time of back-scattered light matches a duration of a laser pulse;
   transmitting the laser pulse with the transmitter to a location within the liquid medium with a predetermined lateral magnification M, longitudinal magnification $M^2$, pulse duration τ, wavelength $\lambda_W$, focused size S and range R such the location is sized to avoid effects of diffractive spreading;

receiving back-scattered light with the receiver as the laser pulse propagates thru the pulse location within the liquid medium;

imaging the location such that the backscattered light that undergoes multiple scattering is minimized;

outputting voltage data based on said imaging step with the photodetector; and processing the voltage data with the controller to make a fit of the voltage data to time dependence of the laser pulse; and providing a diffuse attenuation coefficient of the laser pulse within the liquid medium based on said processing step.

6. The method in accordance with claim 5, said method further comprising the step of:

transmitting a plurality of laser pulses;

transmitting a plurality of laser pulses at different ranges and providing a range resolution of $$\Delta R = \frac{c_W \tau}{2}$$

in order to provide an average of varying laser pulses wherein $c_W$ is the speed of light at a wavelength in the liquid medium of the laser pulse; and determining a beam attenuation coefficient, c, of the liquid medium by $$c = \frac{1}{2(R_2 - R_1)} \ln\left(\frac{\overline{P}_1}{\overline{P}_2}\right)$$

wherein $P_1$ is an average power of the laser pulses from said transmitting a plurality of laser pulses step and $P_2$ is an average power of the laser pulses at said step of transmitting a laser pulse at different ranges.

* * * * *